United States Patent [19]
Tohjoh et al.

[11] Patent Number: 4,856,495
[45] Date of Patent: Aug. 15, 1989

[54] ENDOSCOPE APPARATUS

[75] Inventors: Yoshikazu Tohjoh; Akira Hasegawa, both of Hachioji; Tomoaki Sato, Higashiyamato, Japan

[73] Assignee: Olympus Optical Co., Ltd., Japan

[21] Appl. No.: 263,553

[22] Filed: Oct. 27, 1988

Related U.S. Application Data

[63] Continuation-in-part of Ser. No. 83,712, Aug. 10, 1987, abandoned.

[30] Foreign Application Priority Data

Sep. 25, 1986 [JP] Japan ............................ 61-147037

[51] Int. Cl.$^4$ ............................................. A61B 1/06
[52] U.S. Cl. ..................................................... 128/6
[58] Field of Search ........................ 128/4, 6; 350/445

[56] References Cited

U.S. PATENT DOCUMENTS 4,037,938 7/1977 Yamashita .......................... 350/445
4,660,982 4/1987 Okada .................................. 128/6 X

FOREIGN PATENT DOCUMENTS 57-89711 6/1982 Japan ....................................... 128/6

Primary Examiner—William H. Grieb
Attorney, Agent, or Firm—Ostrolenk, Faber, Gerb & Soffen

[57] ABSTRACT

A first optical adapter is to be detachably mounted on the distal end of an endoscope having an observation optical system and an illumination optical system, in which an aperture diaphragm which has been disposed at a given position within the observation optical system of the endoscope in the past, is disposed instead within an observaiton optical system of the optical adapter such that its optical axis is in agreement with that of the observation optical system for the endoscope. The optical adapter is selected from a set of adapters having different F numbers or the optical adapter is provided with a set of different F number diaphragms which are interchangeable. This enables the F number of the observation optical system of the endoscope apparatus to be changed by merely selecting the appropriate front optical adapter or diaphragm, depending upon brightness of the observation optical system, depth of field and brightness of an object being observed, as well as observation range and view angle of the observation optical system and the like, in order to obtain a clear observation image with optimum brightness.

7 Claims, 5 Drawing Sheets

1

ENDOSCOPE APPARATUS

BACKGROUND OF THE INVENTION

This application is a continuation-in-part of copending application Ser. No. 83,712, filed Aug. 10, 1987, now abandoned and assigned, to the assignee of the instant application. The disclosure of said application Ser. No. 83,712 is incorporated herein by reference.

The present invention relates to endoscope apparatus in general and relates more particularly to an optical adapter for adjusting visual field brightness, which adapter is mounted at the distal end of the endoscope's insertable portion.

In recent years, many endoscopes for medical uses have been capable of observing a visceral cavity by inserting a slender insertable portion of the endoscope into the cavity and, when necessary, making a detailed diagnosis by gathering living tissue with forceps inserted through a forceps channel. Generally industrial endoscopes are used to observe and inspect the interior of boilers, turbines, engines, chemical plants and the like.

A direct-view type endoscope is convenient to use for observation when an affected part is in front of the distal end of the insertable portion in the longitudinal direction thereof. When an internal cavity wall is on the side of a cavity perpendicular to the direction of insertion, a side-view type endoscope is convenient to use for observation. In addition, a different view-angle endoscope can be conveniently used depending upon rough observation in a large view scope or precise observation in a narrow view scope. However, because endoscopes are expensive, it is very uneconomical to keep various endoscopes for observing different objects. To combat such problem, Japanese Laid-Open Patent Application Sho No. 56-85324 discloses a technique for mounting a front optical adapter at the distal end of the insertable portion of an endoscope, which adapter is provided with an optical system to adjust visual field angle and direction.

An endoscope technique has been proposed in which the objective is mounted on the distal end of an endoscope by a non-rotatable connecting means so as to restrict rotation and a connecting portion which won't restrict rotation. The connecting portion cannot be loosened during the focusing operation because the objective is provided with a rotatable focusing means and is connected thereto in a non-rotational manner, with the objective not having focusing means to be connected thereto in a rotational manner.

In general, a field diaphragm is provided in an observation optical system of an endoscope such that there is a wide angle field which can be observed with a fixed focus by enlarging depth of field. The field diaphragm is not interchangeable. When the diaphragm is disposed within a front optical adapter provided on the distal end of an endoscope, the F number of the observation optical system cannot be changed.

For an endoscope in which such a diaphragm is located, in order to enlarge the depth of field, the visual field becomes dark when observing an object at a remote point and, reversely, the visual field may be too bright when observing an object at a near point. In an endoscope which has a small depth of field, without stopping the diaphragm proper brightness can be obtained when observing an object at a remote point but in such a situation brightness grade becomes too great when observing an object at a near point.

In general, the brighter the visual field, the better and the greater will be depth of field, and observation qualities are improved. However, in an endoscope with the fixed focus of a conventional diaphragm, brightness increases and depth of field decreases when an F number of the observation optical system is reduced, and the depth of field increases and brightness decreases when the F number is increased.

SUMMARY OF THE INVENTION

It is an object of this invention to provide an aperture diaphragm located in the observation optical system of an endoscope apparatus to define an F stop number for the optical system. The diaphragm is centered on the optical axis of the observation system and is located between two lenses in the observation system being adjacent to one of these lenses which is between the other lens and the user of the endoscope.

It is an object of the present invention to provide an endoscope apparatus in which there is a front optical adapter or a diaphragm within the front optical adapter, which adapter or diaphragm is selectably interchangeable with an adapter or diaphragm having a different F number so that an F number of an observation optical system is variable in accordance with desirable brightness for the observation optical system in accordance with depth of field, brightness of an object being observed, observation distance and view angle of the observation optical system (focal length), to obtain a clear observation image with optimum brightness An endoscope apparatus according to the present invention comprises an observation optical system adapted to be mounted on the distal end of the insertable portion of an endoscope and a plurality of interchangeable diaphragms which are variable in F number of the observation optical system. Thus, a particular diaphragm is selected in accordance with a brightness of the observation optical system, scope of depth of field, brightness of the object being observed, observation distance and view angle of the observation optical system (focal length).

DETAILED DESCRIPTION OF PREFERRED EMBODIMENTS

Figure 3:
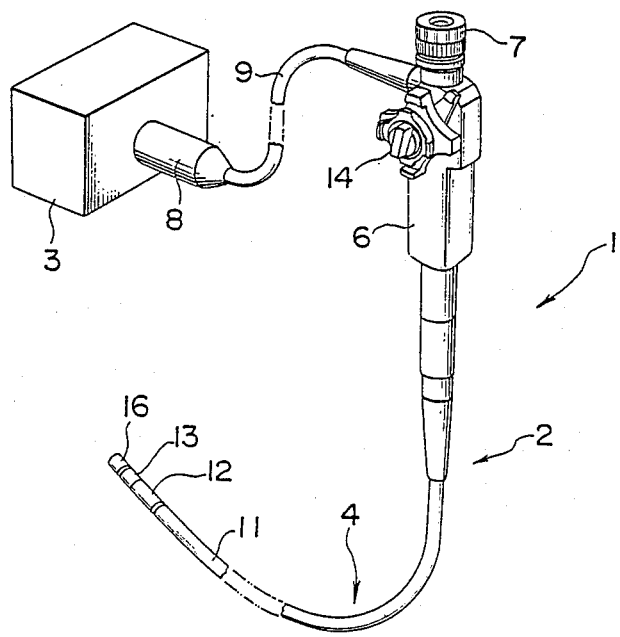

In FIG. 3, endoscope apparatus 1 comprises endoscope 2 and light source 3 for supplying illumination light. Endoscope 2 is provided with a slender and flexible insertable portion 4, for example, and operating portion 6 of relatively large diameter connected to portion 4 at its rear end. Eyepiece portion 7 is disposed at the rear end of operating portion 6, and universal cord 9 extends from the side of operating portion 6. Connector 8 on the front end of universal cord 9 connects the latter to light source 3. Insertable portion 4 comprises a bendable portion 12 connected to the front end of a soft portion 11 provided on the end of portion 4 remote from operating portion 6. Distal end portion 13 is connected to the front of bendable portion 12 and is provided with front optical adapter 16. In a manner known to the art, bendable portion 12 is bendable up and down and right and left by rotating a knob 14 provided on the operating portion 6.

Figure 1:
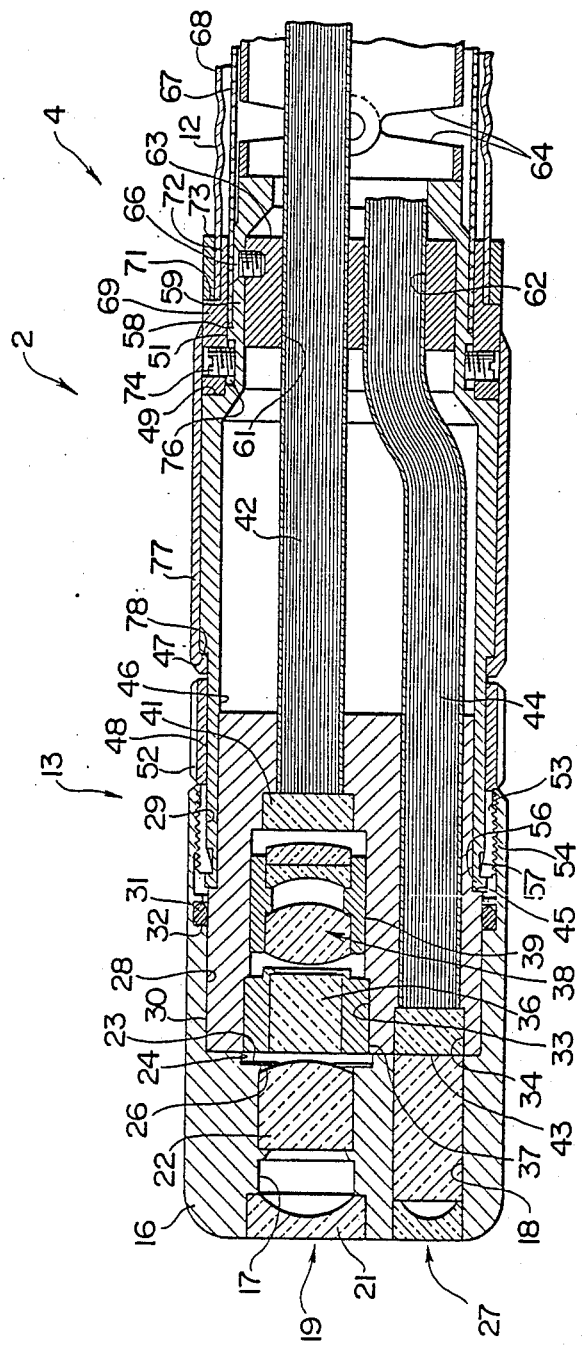
FIGS. 1 to 3 illustrate a first embodiment of an endoscope apparatus constructed according to the present invention, FIG. 1 being a longitudinal sectional view of the distal end of an endoscope, FIG. 2 being a sectional view of a front optical adapter for observing an object at a near point and FIG. 3 being a diagram illustrating an entire endoscope apparatus.

Front optical adapter 16, for observing an object located at a remote point, is generally cylindrical and is formed of a hard material. As seen in FIG. 1, through-hole 17 for observation and through-hole 18 for illumination, both at the distal end of front optical adapter 16, extend parallel to the longitudinal direction of insertable portion 4. Fitted into the front end of through-hole 17 is first lens 21 constituting a view angle changing lens system 19 in the observation optical system. Second lens 22 is fixedly positioned by a step portion at the rear of first lens 21. Disc-shaped diaphragm 26 is fixed so as to abut against step 23 at the front of increased diameter portion 24 at the rear of through-hole 17. Diaphragm 26 provides an optimum F number when an object at a remote point is observed.

Light distribution lens system 27 of an illumination optical system is fixedly fitted into through-hole 18. Recess 28 of circular cross-section is slightly larger in diameter than the outer diameter of substantially cylindrical distal end body 30 provided on distal end portion 13 of insertable portion 4 so that body 30 can be inserted into recess 28. Body 30 projects from the rear end surface of front optical adapter 16 such that the center line of the front optical adapter 16 is aligned with the center line of insertable portion 4. Thread 29 is formed on the inner peripheral rear end of the recess 28 and groove 32, formed at the front inner peripheral surface of thread 29, receives ring-shaped watertight member 31, constituted by an O-ring.

Front end body 0 which is inserted into recess 28 is provided with through-hole 33 for observation and through-hole 34 for illumination. Both holes 33 and 34 extend parallel with the longitudinal direction of insertable portion 4.

First lens frame 37 into which optical rod 36 is inserted, and second lens frame 39 into which objective system 38 is inserted at the rear of the first lens frame 37, are fitted in through-hole 33. Further, the front or incident end surface of image guide 42, having cover glass 41 thereagainst, is fixedly inserted into distal end body 30 at an image forming position in objective system 38. Cover glass 43 for the front end surface of light guide 44, is inserted into the front end of through-hole 34.

Step portion 45 is formed at the outer peripheral rear portion of distal end body 30 so that the diameter of the latter is reduced towards the rear end thereof. The front end surface of cylinder-shaped cover member 46 of distal end portion 13 abuts step portion 45. Reduced diameter portion 48, whose diameter decreases forwardly of step portion 47, is formed in the front of the outer peripheral surface of cover member 46, and reduced diameter portion 51, whose diameter decreases rearwardly of step portion 49, is formed in the rear of the outer peripheral surface of cover member 46

Connecting ring 52 has the same outer diameter as front optical adapter 16 and surrounds reduced diameter portion 48 so as to be rotatably mounted thereon. Threaded portion 54 having longitudinal slits 53 is located at the front outer periphery of ring 52 add mates with threaded portion 29 on the rear inner surface of front optical adapter 16. Inward projection 56 at the front of ring 52 is entered into recess 57 on the front outer periphery of cover member 46, so that ring 52 is captured on cover member 46.

Cylindrical ring stop 63, disposed within the reduced diameter rear portion 59 of cover member 46, is provided with and secured by screw 66 is provided with, bore 61 through which image guide 52 extends and bore 62 through which light guide 44 extends. In a manner known to the art, a plurality of substantially ring-shaped joint pieces 64 are pivotally connected within bendable section 12 of insertable portion 4. In particular, joint pieces 64 are covered by flexible tube 67 that is fitted on the reduced diameter portion 59 so as to abut against outward step 58 thereof. The outer surface of the tube member 67 is surrounded by protection sheath 68 made of a mesh tube instructed of fine metal thread. The most forward of these joint pieces 64 is fitted on the rear of ring stop 63 and is secured by screw 74.

The front end of protection sheath 68 is fitted onto reduced diameter portion 72 of collar 69. Portion 72 extends rearward from step 71 of collar 69. This portion of collar 69 forward of step 71 has an outer diameter equal to or slightly less than that of cover member 46. The front end outer periphery of sheath 68 which covers collar 69 is surrounded by and secured to ring 73, as by soldering. Ring 73 extends rearward from step 71 and has an outer diameter essentially equal to that of collar 69, while the inner diameter of ring 73 is such that sheath 68 is clamped against the outside of member 69.

A plurality of locking screws 74 are threadably fitted onto the front of collar 69 and pass radially therethrough, the through recess 76 provided on the outside of reduced diameter portion 51 of cover member 46 into clamping engagement with the outside of cover member 46 to secure sheath 68 to distal end 13. In order to prevent the screws 74 from falling off, they are covered by cylindrically shaped member 77 that is loosely fitted on the outside of cover member 46. The outer diameter of member 77 is essentially the same as that of front optical adapter 16. Inwardly extending lip 78 at the front of member 77 abuts step portion 47 provided on the cover member 46.

Figure 2:
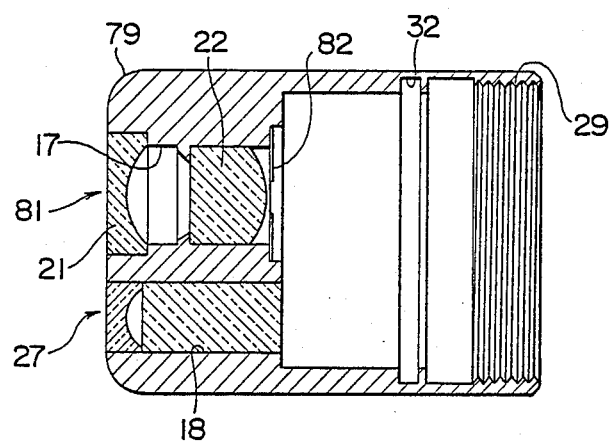

Front optical adapter 79 (FIG. 2) for observing an object at a near point is constructed with the same outer configuration as that of front optical adapter 16 (FIG. 1) for observing an object at a remote point, and is mountable on distal body 30. View angle changing lens system 81 provided on adapter 79 acts together with objective system 38 to focus on an object at a near point. Diaphragm 82 having a large F number and disposed rearwardly of view angle changing lens system 81, is provided so that the quantity of light is optimum for observing an object at a near point.

In operation, front optical adapter 16 provided on distal end body 30 of the endoscope 2 forms an observation optical system by combining objective system 38 and view angle changing lens system 19 disposed at the front optical adapter 16. In the case of a fixed focus type optical system, for example, the optimum focus position is set on the remote point side. Diaphragm 26 provides an aperture for optimum brightness when an object at a remote point is observed. Upon completion of such conditions, insertable portion 4 is inserted in the vicinity of the observation position.

Illumination light emitted from light distribution lens system 27 provided on the front of optical adapter 16 is projected onto an object at a remote point. Reflected light from the remote object passes through view angle changing lens system 19 and, utilizing objective system 38, forms an image on the incident end surface of the image guide 42. This light has been stopped by diaphragm 26 so as to be at on optimum level upon reaching image guide 42. The optical image thus formed is transmitted through image guide 42 to eyepiece 7, enabling an operator to observe the image under optimum brightness. Since this observation optical system is able to obtain a depth of field larger than that of a system in which the diaphragm 26 is not provided, it is possible for an operator to obtain an observation image that is focused over a wide range.

When an object at a near point is to be observed, front optical adapter 16 is removed and replaced by front optical adapter 79 having view angle changing lens system 81 that feeds objective system 38.

Illuminating light emitted from light distribution lens system 27 is projected onto an object at a near point and reflected light impinges onto view angle changing lens system 81. Since the object being observed is near, the incident light is too intense, but it is stopped by diaphragm 82 and then passes through objective system 38 to form an image with suitable light intensity on the incident end surface of image guide 42. The optical image thus formed is transmitted through image guide 42 to form an observation image at eyepiece 7. The observation image is of optimum brightness because excess light is stopped by diaphragm 82. Further, a broad depth of field results from utilization of stop diaphragm 82 resulting in a clear observation image at eyepiece 7.

Figure 4:
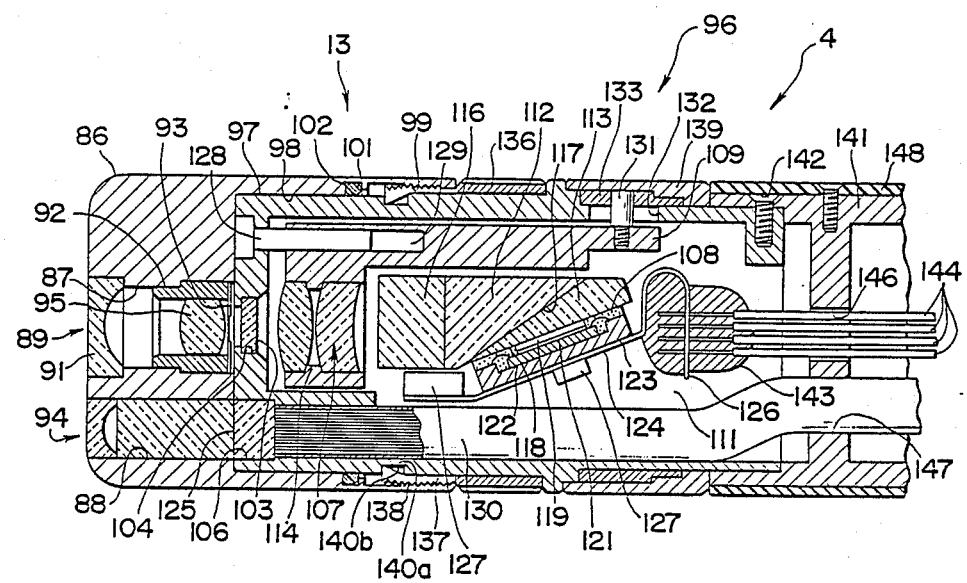
FIGS. 4 and 5 illustrate a modification of the first embodiment with FIG. 4 being a longitudinal sectional view of the distal end of an endoscope and FIG. 5 being a side elevation of the guide mounting for a movable frame.
Figure 5:
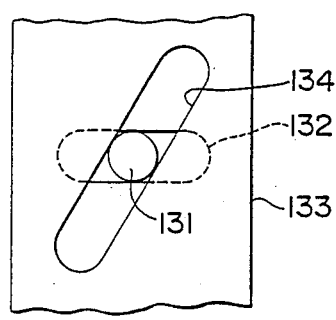

FIGS. 4 and 5 illustrate a modification of the first embodiment (FIGS. 1–3), in which the present invention is applied to an electronic endoscope having a focus adjusting mechanism in an observation optical system. In FIG. 4 front optical adapter 86, for observing an object at a remote point, is removably mounted on distal end 13 of electronic endoscope 96. Through-hole 87 for observation and a through-hole 88 for illumination extend through optical adapter 86 parallel to the longitudinal axis of insertable portion 4.

First lens 91 of view angle changing lens system 89 is fitted onto the front end of observation through-hole 87. A second lens 95, fitted onto lens frame 92, is disposed rearwardly of first lens 91. Clear diaphragm 93, having a large F number and disposed on the rear end surface of lens frame 92, is utilized to obtain a proper brightness level to observe an object at a remote point.

Light distribution lens system 94 is fixedly fitted into the illumination through-hole 88. Circular recess 98 at the rear end of front optical adapter 86 receives substantially cylindrical distal end body 97 of electronic endoscope 96. The center line of front optical adapter 86 is in agreement with that of the insertable portion 4 At its rear end the inner periphery of recess 98 is provided with threaded portion 99. Ring-shaped interior groove 102 at the front of threaded portion 99 receives watertight member 101, in this case an O-ring.

Cover glass 103 is fixed at the front end of distal end body 97 which is inserted into the recess 98. Observation window 104, having an optical axis that coincides with that of the view angle changing lens system 89, and illumination through-hole 106 are provided at the front of distal end body 97 in parallel with the longitudinal axis of insertable portion 4. Recess 111 is provided to the rear of observation window 104 to house movable frame 109, square optical low-pass filter 116, first prism 112, second prism 113 and solid-state image pickup package 108. Objective system 107 is fixedly positioned in observation through-hole 114 at the front of movable frame 109 and is disposed such that the optical axis of objective system 107 is at the center of observation window 114. Optical low-pass filter 116 is disposed to the rear of objective system 107 and centered on the optical axis thereof, with front and rear end surfaces of filter 116 being perpendicular to the optical axis of objective system 107. The front end surface of first prism 112 is secured to the rear end surface of low-pass filter 116, and the rear end surface 117 of first prism 112 is inclined with respect t the optical axis of objective system 107. Second prism 113 is a shallow wedge having its front end surface secured to inclined surface 117, and with first prism 112 having its thinnest portion positioned more forward than the remainder of prism 113. Rear end surface 118 of second prism 113 is also inclined with respect to the longitudinal direction of insertable portion 4. Seal glass 119 provided on the image pickup surface side of image pickup package 108 abuts rear end surface 118. Color filter array 21 is disposed to the rear of seal glass 119 and solid-state image pickup chip 122 is disposed on the opposite side of array 121. Chip 122 is secured to package base 123 formed of insulating material, such as an insulating ceramic, and is sealed thereto with a suitable resin.

Substrate 124 is mounted on the side of base 123 opposite to chip 122. Image pickup package 108 and substrate 124 are secured to the movable frame 109 by an adhesive. The rear end of the substrate 124 mounts a cable connector 126 and electronic parts assembly 127 is mounted on the front end of substrate 124.

The exit end surface light guide 130 which supplies illumination light to the observation position abuts the rear end surface of cover glass 125 that is disposed in illumination through-hole 106. Guide bar 128 extends rearward from the front end of distal end body 97 and enters guide hole 129 at movable frame 109.

Pin 131 is threadably mounted on the rear end of the movable frame 109 and projects radially outward therefrom, through longitudinally extending guide slot 132 (FIG. 5) and through cam slot 134 that is inclined with respect to the longitudinal direction. Cam slot 134 is in cam ring 133 which is rotatably mounted on the outer periphery of distal end body 97.

Connector ring 136, having the same outer diameter as that of the front optical adapter 86, is rotatably mounted on the center portion of distal end body 97. Threaded portion 138 at the front outer periphery of connector ring 136 is provided with a plurality of longitudinal slits 137 and mates with threaded portion 99 provided on the rear inner periphery of front optical adapter 86. Projection 140a on the front inner periphery of connector ring 136 is entered into recess 104b provided on the central outer periphery of distal end body 97. Range ring 139 is mounted on the cam ring 133 at a position to the rear of connector ring 136, and has the same outer diameter as that of front optical adapter 86.

Connecting member 141, secured to the front end of a joint piece composing a bendable portion (not shown), is mounted rearwardly of range ring 139 and is secured to distal end body 97 by a plurality of screws 142. Insulated cable conductors 144 extend rearward from reinforcing member 143 of cable connector 126 and pass through passage 146 in member 141. The latter is also provided with passage 147 through which light guide 130 passes Protection sheath 148 covers the outside of connecting member 141.

When electronic endoscope 96 is being operated illumination light emitted from light distribution lens system 94 of front adapter 86 is projected onto an object at a remote point. The reflected light from the remote object passes through the view angle changing lens system 89 and is stopped by the diaphragm 93 so as to have the optimum amount of light for forming an image on the image pickup surface of solid-state image pickup chip 122, which image is transmitted through objective system 107 to chip 122. Such optical image is transformed by photoelectrical conversion to an image signal which is read out by a drive signal, is operated on by a signal treating circuit and is then displayed as an observation image by a monitor (not shown). Because diaphragm 93, provided in the observation optical system that includes lens systems 89 and 107, has a bright F number a shallow depth of field results so that focusing may be loose depending upon the position of a remote object being viewed. In this case, movable frame 109 is moved in the longitudinal direction of insertable portion 4 by rotating range ring 139 to adjust objective lens system 107 to obtain optimum focusing As a result, the observation optical system (89, 107) is positioned at the optimum focus point despite working with a short depth of field. Accordingly, an operator is able to observe a clear image with brightness being optimum.

When an object at a near point is to be observed, front optical adapter 86 for observing an object at a remote point is removed and replaced by a front optical adapter having a light stop diaphragm for observing an object at a near point. Thus, it is possible to obtain an observation image with optimum brightness as well as with a large depth of field by utilizing an appropriate diaphragm.

Diaphragm 93 has a bright F number in order to brighten the visual field. Because the observation position is remote, and the depth of field is reduced with a bright F number, an observation image may be defocused. It is possible to eliminate such disadvantages by bringing the observation optical system into the optimum focus position by adjusting the longitudinal position of frame 109 to obtain a clear observation image.

Figure 6:
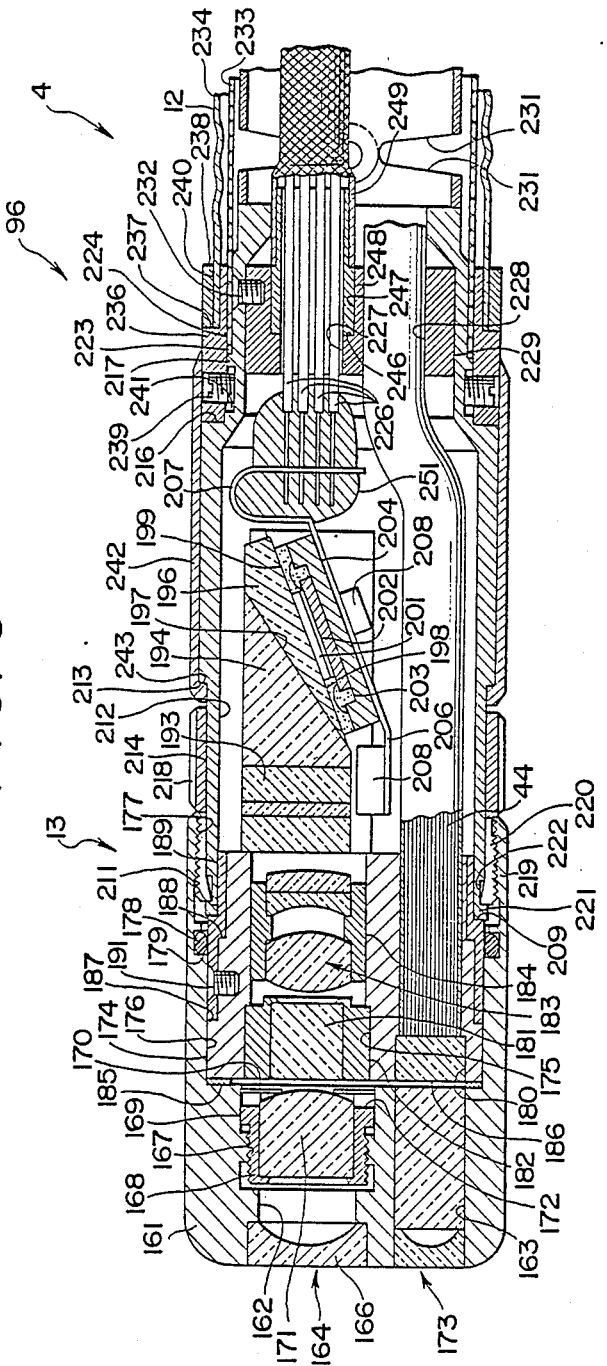
FIG. 6 illustrates another modification of the first embodiment and is a longitudinal sectional view of the distal end of an endoscope.

In FIG. 6 a substantially cylindrical front optical adapter 161 whose housing is formed of a hard material, is provided on the front end of insertable portion 4 of electronic endoscope 96. Through-hole 126 for observation and through-hole 163 for illumination are formed on the front end of adapter 161 and extend parallel to the longitudinal direction of insertable portion 4.

First lens 166 of view angle changing lens system 164 is fitted into the front end of observation through-hole 162, and second lens 171 of lens system 164 disposed rearwardly of first lens 166 is fitted into lens frame 169. The latter includes male thread portion 168 which mates with female thread portion 167 provided on the inner periphery of observation through-hole 162, so that second lens 171 is movable in the longitudinal direction. A plurality of radially extending grooves 172 in the rear end surface of lens frame 169 serve as a means that is engageable by a tool (not shown) that is used to rotate lens frame 169.

Diaphragm 170, having a bright F number so as to give the optimum brightness to observe an object at a remote point, is disposed adjacent the rear end surface of lens frame 169. Light distribution lens system 173 is fixedly inserted into illumination through-hole 163. Substantially cylindrical distal end body 174 of electronic endoscope 96 is insertable into circular recess 176 at the rear end of front optical adapter 161. The latter extends through an aperture in spacer 185 into recess 175 and is positioned such that the center line of the adapter 161 is in agreement with that of insertable portion 174.

Interiorly threaded portion 177 is disposed at the rear end of recess 176. Ring-shaped watertight member 178, such as an O-ring, is disposed in groove 179 at the front of the threaded portion 177 in groove 179. Through-hole 175 for observation and a through-hole 180 for illumination are provided on distal end body 174 which is inserted into the recess 176, in parallel with the longitudinal direction of insertable portion 4.

First lens frame 182 into which optical rod 181 is fixedly inserted is disposed in front of second lens frame 184 into which objective system 183 is inserted. Lens frames 182 and 184 are disposed in observation through-hole 175. Cover glass 186 is fitted into the front end of the illumination through-hole 180, and the end surface of light guide 44, which extends through insertable portion 4, is in abutment with the rear end surface of cover glass 186.

Step portions 187 and 188 are formed on the outer peripheral rear end of distal end body 174 and the front end surface of cylindrical prism frame 189 abuts against step portion 187. The outer diameter of prism frame 189 is equal to the inner diameter of distal end body 174, is inserted into distal end body 174 and is fixed thereto by a plurality of screws 191.

Square low-pass optical filter 193, first prism 194 and second prism 196 constitute a light guide means that is at the rear end of prism frame 189. Low-pass filter 193 is disposed with its front and rear end surfaces perpendicular to the optical axis of objective lens system 183. The front end surface of first prism 194 is fixed to the rear end surface of low-pass filter 193, and inclined surface 197 is formed on the rear end side of first prism 194. Second prism 196 is a relatively thin wedge having its front surface fixed to inclined surface 197. Rear end surface 198 of second prism 196 is inclined with respect to the longitudinal direction of insertable portion 4. Seal glass 201 disposed on the image pickup package 199 abuts rear end surface 198 of second prism 196 and is fixed thereto so as to be inclined with respect to the longitudinal direction of insertable portion 4. Color filter array 202 and solid-state image pickup chip 203 are disposed behind seal glass 201 and chip 203 is fixed to package base 204, formed of ceramics.

Substrate 206 is secured to package 199 behind the image pickup side thereof. Package 199 and/or substrate 206 are secured to the prism frame 189 by adhesion. The bent rear end of the substrate 206 forms the core of cable connector 207. Electronic parts 208 are arranged on opposite sides of the substrate 206.

Step 209 on the rear outer periphery of prism frame 189 forms a reduced diameter portion 211. Substantially cylindrical cover member 212 for substrate 206 has its front end surface abutting step 209. Reduced diameter front portion 214 and the front outer periphery of cover member 212 is formed by step portion 213. From step 216 rearward, cover member 212 is of reduced diameter which is interrupted by very shallow outward step 217.

Connecting ring 218, having the same outer diameter as that of the front adapter 161, is rotatably mounted on the outer periphery of reduced diameter portion 214. Front outer periphery portion 219 of connecting ring 218 is provided with a plurality of longitudinal slits 220, and 219 mates with threaded portion 177 at the rear end inner periphery of front adapter 161. Projection 221 on the front inner periphery of connecting ring 218 extends into recess 222 provided on the front outer periphery of cover member 212.

Cylindrical ring stop 229 is provided with hole 227 through which a plurality of cable conductors 226 extend rearward from cable core connector 207. Light guide 44 extends through hole 228 in ring stop 229. The latter is fixedly positioned in the rear reduced diameter of the cover member 212 and is secured in this position by a set screw 232. The most forward joint piece 231, in a flexible stack (not shown) formed by a plurality of joint pieces 231, is substantially of ring shape and is fixed to the rear of cover member 212. This stack of joint pieces 231 is covered by flexible tube member 233 having a front end that extends through narrow space 224 into abutment with step portion 233. The outer periphery of tube member 233 is covered with protection sheath 234 formed from a braided tube of fine metal threads.

Cylindrical fixed member 236 having an outer diameter equal to or less than that of cover member 212 is fitted on the front end of protection sheath 234, with the front end of the latter abutting step portion 237. The front of sheath 234 is fitted over reduced diameter portion 240 of member 236 and is captured by ring 238 which is connected to sheath 234 by a fixing operation, such as soldering. A plurality of radially extending screws 239 provided on the front of fixed member 236 extend through recess 241 and abut reduced diameter portion 217 of cover member 212 to connect sheath 234 with distal end 13. In order to prevent screws 239 from falling out, member 242 is loosely fitted on the outer periphery of cover member 212.

The outer diameter of member 242 is equal to that of front optical adapter 161. A step portion 243 is provided at the front inner periphery of member 242 so as to abut against step portion 213 provided on cover member 212.

Increased diameter portion 247 of cable core passage 227 extends to the rear from step 246. Cylindrical wire lock 248 is fitted into increased diameter portion 247. Braided wire shield 249 which covers the outer periphery of cable conductors 226 is fitted on the outside of reduced diameter portion of wire lock 248 and is fixed by soldering or by a conductive adhesive. Cable conductors 226 pass through wire lock 248 and are secured to reinforcing member 251 on cable connector 207. Cable core 226 is also fixed to wire lock 248 by insulating adhesives or the like.

In the modification shown in FIG. 6 the diaphragm 170 has a brightness rating suitable for observing objects at both near and remote locations, in a manner similar to the modification shown in FIG. 4 in which front optical adapter 86 is provided for an electronic endoscope having a focusing function It is possible to obtain a clear observation image by selectively disposing spacer 185 so that the observation optical system assumes the optimum focus point. The correct spacer 185 is easily selected. If it is desired to observe an object with the observation optical system on which the front optical adapter having a narrow view angle is mounted, the observation area at a comparatively remote position is enlarged. In this case, often there appears to be sufficient illumination light. Accordingly, the diaphragm in the front optical adapter is opened to make the F number of the observation optical system bright, so that it is now possible to obtain a properly clear image even with an observation area at a remote position. However, with the observation optical system having a narrow view angle (long focal length), depth of field becomes small when operated just as described above, so that it is possible to observe an object by darkening the F number of the observation optical system with the diaphragm in the front optical adapter stopped for observation of an area having sufficient brightness even when the object is remote.

In the observation optical system including a front optical adapter having wide view angle, depth of field is large due to the wide view angle. To obtain a depth of field equivalent to an observation optical system of a narrow view angle, it is possible to make the F number bright as compared with the observation optical system having a narrow view angle and to obtain a properly clear observation image even when observing a dark area. In addition, it is possible to maintain an observation image in focus without the necessity of focusing from a near point to a remote point.

Figure 7:
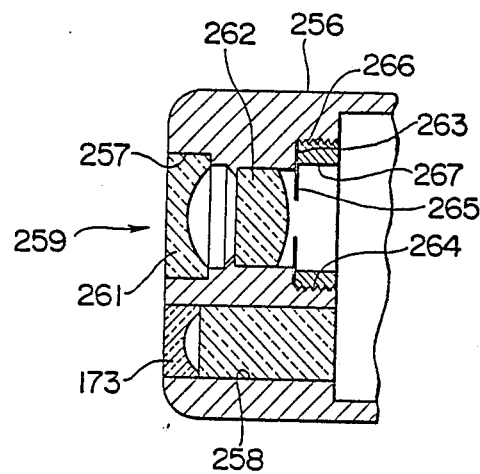
FIGS. 7 and 8 illustrate a an endoscope apparatus constructed according to the present invention, FIG. 7 being a fragmentary sectional view of a front optical adapter, FIG. 8(*a*) being an explanatory view of a diaphragm for observing a remote point and FIG. 8(*b*) being an explanatory view of a diaphragm for observing a near point.

In FIG. 7, substantially cylindrical front optical adapter 256 is formed of a hard material. Observation through-hole 257 and an illumination through-hole 258 extend from the front end of adapter 256 in parallel with the center line of adapter 256. First lens 261 of view angle changing lens system 259, is fixedly fitted into the front end of observation through-hole 257, and second lens 262 is fixedly positioned by a step rearwardly of first lens 261.

Female threaded portion 264 extends to the rear from step portion 263 and is formed in the enlarged inner peripheral portion of observation through-hole 259 to the rear of second lens 262. Diaphragm disc 265 has one surface abutting step portion 263 at the front of female threaded portion 264. In addition, ring-shaped diaphragm lock 267 provided with male threads 266 on the outer periphery thereof is inserted into female threaded portion 264 so as to press diaphragm 265 against step 263. Light distributing lens system 268 is fixedly inserted into illumination through-hole 258.

Figure 8A:
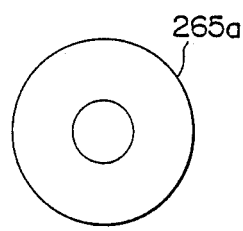
Figure 8B:
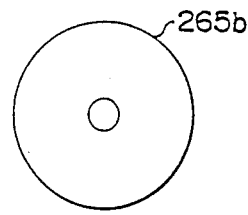

FIGS. 8(a) and 8(b) illustrate two different versions for diaphragm 265. That is the central opening of diaphragm 265a is larger than the central opening of diaphragm 265b. Thus, diaphragm 265a is of a relatively bright F number for observing a remote point and diaphragm 265b is of a relatively dark F number for observing a near point. The particular diaphragm 265 is selected to obtain an observation image of optimum brightness.

Other structures, functions, and effects of the later embodiments described herein are the same as those of the first embodiment From the foregoing, it will now be recognized by those skilled in the art that it is possible to obtain the same effects with a fiber scope in the first embodiment as well as with a fiber scope and an electronic endoscope in the modification thereof. In addition, it is possible to easily and correctly selectively select the required diaphragm value by clearly marking respective F numbers on the front optical adapters in the first embodiment and on interchangeable diaphragms in the second embodiment.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. An optical adapter for an endoscope to be detachably mounted on the distal end of the endoscope, said endoscope including an observation optical system and an illumination optical system, comprising:
   an observation optical system;
   an illumination optical system; and
   an aperture diaphragm disposed within said observation optical system of said optical adapter such that its optical axis is in agreement with that of the observation optical system of the endoscope.

2. An optical adapter as set forth in claim 1 in which the observation optical system of said optical adapter includes first and second lenses substantially spaced along the optical axis of said optical adapter;
   said lenses being positioned so that a user of the endoscope is closer to the second lens than to the first lens;
   said aperture diaphragm being disposed between said lenses and adjacent said second lens.

3. Endoscope apparatus including an optical adapter to be detachably mounted on the distal end of an endoscope, said endoscope including an observation optical system and an illumination optical system, and said optical adapter including;
   an observation optical system and an illumination optical system;
   an aperture diaphragm disposed within the observation optical system of said optical adapter such that its optical axis is in agreement with that of the observation optical system of the endoscope; and
   said aperture diaphragm of said observation optical system of said optical adapter being detachably mounted.

4. An endoscope apparatus as set forth in claim 3 including a plurality of said aperture diaphragms each having a different F number;
   each of said aperture diaphragms being selectively insertable in the observation optical system of the optical adapter to provide optimum viewing of an image.

5. An endoscope apparatus as set forth in claim 3 including a plurality of said optical adapters;
   a plurality of said aperture diaphragms each of a different F number; a different one of said aperture diaphragms being in each of said optical adapters whereby optimum viewing of an image is obtained by mounting a selected one of said optical adapters at the distal end of said endoscope.

6. An endoscope apparatus as set forth in claim 3 in which said endoscope is a fiberscope.

7. An endoscope apparatus as set forth in claim 3 in which said endoscope is an electronic scope.

* * * * *